US007588886B2

(12) United States Patent
Young et al.

(10) Patent No.: US 7,588,886 B2
(45) Date of Patent: Sep. 15, 2009

(54) PROCESS FOR THE ENUMERATION AND IDENTIFICATION OF MICROORGANISMS

(75) Inventors: Barbara Young, Needham, MA (US); Esther Presente, Littleton, MA (US); Andrew Sage, Littleton, MA (US)

(73) Assignee: Millipore Corporation, Bedford, MA (US)

( * ) Notice: Subject to any disclaimer, the term of this patent is extended or adjusted under 35 U.S.C. 154(b) by 520 days.

(21) Appl. No.: 10/181,517

(22) PCT Filed: Jan. 26, 2001

(86) PCT No.: PCT/US01/02682

§ 371 (c)(1), (2), (4) Date: Jul. 15, 2002

(87) PCT Pub. No.: WO01/59157

PCT Pub. Date: Aug. 16, 2001

(65) Prior Publication Data

US 2003/0003540 A1  Jan. 2, 2003

(51) Int. Cl.
*C12Q 1/68* (2006.01)
*C07H 21/04* (2006.01)

(52) U.S. Cl. ............... 435/6; 536/24.31; 536/24.32

(58) Field of Classification Search ............... 435/6, 435/8, 29, 39, 243, 297.1; 210/295, 615; 536/24.31, 24.32
See application file for complete search history.

(56) References Cited

U.S. PATENT DOCUMENTS 4,677,064 A * 6/1987 Mark et al. ............... 435/69.1
5,624,815 A * 4/1997 Grant et al. ............... 435/30
5,627,042 A * 5/1997 Hirose et al. ............... 435/8
6,280,946 B2 * 8/2001 Hyldig-Nielsen et al. ...... 435/6
6,465,201 B1 * 10/2002 Presente et al. ............... 435/8
2001/0010910 A1 * 8/2001 Hyldig-Nielsen et al. ...... 435/6

FOREIGN PATENT DOCUMENTS

| JP | 04-104799 | 4/1992 |
| JP | 08-131199 | 5/1996 |
| JP | 11-137293 | 5/1999 |
| WO | 95/32305 | 11/1995 |
| WO | WO9955916 A | 4/1999 |

OTHER PUBLICATIONS

"Direct enumeration of enteric bacteria in food, beverages and water by in situ hybridization to 16S ribosomal RNA." Abstracts of the general meeting of the American Society for, vol. 99, 1999, p. 516 XP002199783 99$^{th}$ General Meeting of the American Society for Microbiology; Chicago, Illinois, USA; May 30-Jun. 3, 1999.

* cited by examiner

*Primary Examiner*—Kenneth R. Horlick
*Assistant Examiner*—Joyce Tung
(74) *Attorney, Agent, or Firm*—Nields, Lemack & Frame, LLC

(57) ABSTRACT

A test for the detection, enumeration and identification of microorganisms in a fluid sample is taught. The test uses a filter through which a fluid sample is passed and onto which organisms within the fluid are deposited. It is then incubated on a growth medium and thereafter subjected to a presence absence test for organisms using an ATP/bioluminescence test. The same sample and filter is then subjected to a PNA probe assay for targeted organisms. Optionally, the locations of the organisms detected by each test can be compared with each other to determine the possibility of false positives and their elimination from the test results.

11 Claims, 1 Drawing Sheet

PROCESS FOR THE ENUMERATION AND IDENTIFICATION OF MICROORGANISMS

The present invention relates to a process for enumerating and then identifying microorganisms. More particularly, it relates to a process for enumerating and identifying microorganisms on a membrane device.

BACKGROUND OF THE INVENTION

The traditional method of determining the presence or absence of microorganisms in liquids such as water, food products such as juices, or pharmaceuticals has been to filter the fluid through a suitable membrane to trap any microorganisms present in the fluid on the surface of the membrane. The membrane is then placed on a growth media plate such as a Petri Dish filled with agar or other suitable media and then incubated for several days to allow colonies to develop from the captured organisms. The plates are then removed and examined visually so that the number of colonies present can be counted. If the number is high enough further tests can be conducted to determine exactly what organisms are present. (Often the mere presence of organisms is not in and of itself an indication that the fluid is unsafe and further work to identify the specific organisms is required.).

Recently, molecular tests such as DNA arrays, nucleic acid amplification and nucleic acid sequencing have been introduced. Traditional identification is done by using selective media and a variety of biochemical tests.

It is known that the simple enumeration of such organisms can be expedited using an ATP-bioluminescence test, such as is taught by U.S. Pat. No. 5,627,042.

It has also been suggested that one may use PNA probe assays to detect the presence and number of specific microorganisms. See U.S. Pat. No. 5,773,571. One drawback to the use of this system is the presence of spots that do not arise from the presence of microorganisms (false positives). Something, yet undetermined, causes the generation of a signal indicating the presence of a target organism when further investigation reveals that in fact no organism is present in that location. These are probably caused by nonspecific binding of probe molecules to the membranes. This renders the test by itself unreliable, as often the detection of even one target organism is enough to fail the fluid being tested.

Further, none of these tests have been able to detect the presence of low levels of contaminating organisms in large volumes of fluids, and rapidly identify the organisms of concern with the same sample and in relatively short time.

What is needed is a simple process to combine the best of both processes with the same sample to determine the number of total organisms present as well as the number of those that are of concern.

The present invention provides such a process.

SUMMARY OF THE INVENTION

The present invention relates to a process for the enumeration and identification of specific species of microorganisms in large volumes of fluid using first an enumeration test such as an ATP-bioluminescence assay or fluorescence indication test to enumerate the total number of organisms and then a PNA probe assay or assays to determine the presence of selected or targeted organisms. A key attribute of the present process is that the same membrane and organism sample is used for both tests. This allows for the rapid detection and identification of organisms that are present by only making and incubating one sample for both tests. Moreover, by using the same sample and membrane for both tests, one can eliminate any false positives by comparing the locations of the organisms indicated by each test relative to one or more registration marks and eliminating those that fail to appear at the same location in both tests.

It is an object of the present invention to provide a process for enumerating and identifying microorganisms comprising:

a) filtering a liquid sample through a membrane suitable for the retention of microorganisms, b) incubating the membrane with any microorganisms, c) applying an enumeration test to the surface of the membrane to enumerate the microorganisms which are present, and counting the number present, d) applying a PNA hybridization to determine the presence/absence of one or more specified microorganisms, and counting the number detected.

It is another object of the present invention to provide a process for enumerating and identifying microorganisms comprising:

(a) filtering a liquid sample through a membrane suitable for the retention of microorganisms, (b) incubating the membrane with any microorganisms, (c) applying an enumeration test to the surface of the membrane to enumerate the microorganisms which are present, and counting the number present, (d) applying a PNA hybridization to determine the presence/absence of one or more specified microorganisms, and counting the number detected, and (e) comparing the location of the organisms detected by (c) with those detected by (d) and eliminating from the analysis those which are not found in the same location by each test.

It is a further object of the present invention to provide a process for enumerating and identifying microorganisms comprising:

(a) filtering a liquid sample through a membrane suitable for the retention of microorganisms and which has a registration mark to indicate a specific location on the membrane, (b) incubating the membrane with any microorganisms, (c) applying an enumeration test to the surface of the membrane to enumerate the microorganisms that are present, and counting the number present, (d) applying a PNA hybridization to determine the presence/absence of one or more specified microorganisms, and counting the number detected, and (e) comparing the location of the organisms detected by (c) with those detected by (d) by comparison to the registration mark and eliminating from the analysis those which are not found in the same location by each test.

IN THE DRAWINGS

DETAILED DESCRIPTION OF THE SPECIFICATION

The present invention relates to a process for the rapid enumeration and identification of microorganisms in fluids or soluble solids such as powders, salts, creams, tablets, etc.

Such fluids include but are not limited to water, potable or otherwise, dairy such as milk, beer, wine, soft drinks, fruit juices, pharmaceuticals, parenterals, bacterial air counts, etc.

Figure 1:
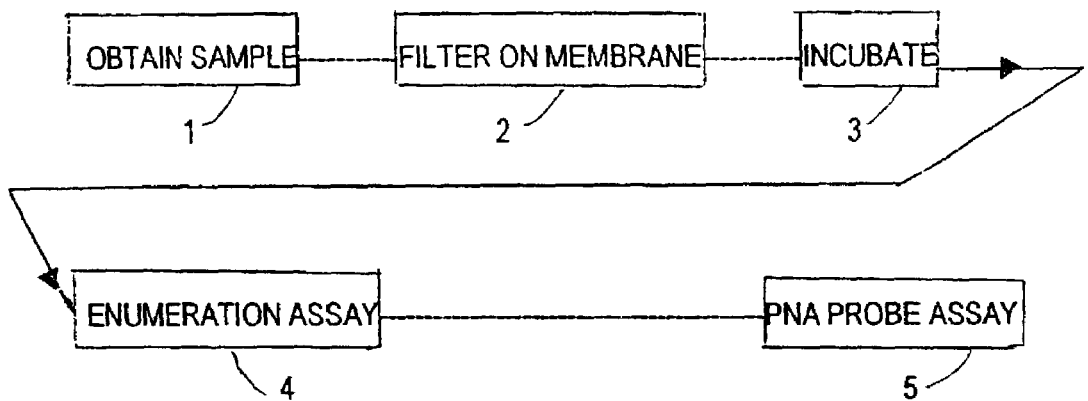
FIG. 1 shows a block diagram of a preferred embodiment of the present invention.

FIG. 1 shows a first preferred process according to the present invention. In this process, as the first step 1, a sample in fluid form is obtained from the product to be diagnosed. For example, in environmental sampling, such as a water supply, a sample of water from the river, well or reservoir is obtained. For a food or pharmaceutical product, a sample is taken from the stock (typically this is the finished stock although it need not be so). If in liquid form it is simply used as is or may if necessary due to viscosity be diluted with deionized water. If in solid form, it is dissolved or dispersed in a suitable liquid, typically water or a buffer or other such media that doesn't kill or unduly stress organisms that are present.

It is then filtered through a membrane filter in the second step 2 and the filter is then placed on to a growth medium such as agar (typically contained in a Petri Dish) and incubated as the third step 3 to allow microcolonies (visible using ATP bioluminescence and imaging, but not visible by eye) to arise from the trapped organisms.

A preferred device for holding the filter is a MIL-LIFLEX™ filter funnel having a 50 mm diameter and a 100 ml capacity, available from Millipore Corporation of Bedford, Mass. Other membrane holders such as glass or stainless steel filter holders or funnels may be used instead. Such devices are well known and available from a variety of sources including Millipore Corporation of Bedford, Mass. and Fisher Scientific, Inc, of Pittsburgh, Pa. A preferred membrane is a MicroStar™ filter, available from Millipore Corporation of Bedford, Mass. This filter is a 0.45 nominal pore size PVDF filter having a series of hydrophilic compartments separated by hydrophobic partitions that extend through the entire depth of the filter. Other filters that are useful in this invention include EZ-Pak™ filters, S-Pak™ filters, S-Pak™ Plus filters and AO™ or SO™ filters, available from Millipore Corporation of Bedford, Mass.

The filter/growth medium is incubated in the third step 3 for a short period of time, typically from 1 to about 24 hours. The length of incubation depends upon the accuracy needed by the test, the rate of growth of the organisms to be detected, the stress to which the organisms have been subjected (the more stress imposed on an organism, the more incubation time is necessary), the type of organism to be detected and the sensitivity of the test used to determine the presence of that organism (the less sensitive the test, the longer the incubation time to ensure that the colony of the target organism has grown to a suitable size), the desired speed of the test vs. the accuracy of the test results and other such factors. The temperature for incubation can be from about room temperature (24° C.) to about 40° C. Higher or lower temperatures may be used depending upon the organism(s) that one wishes to detect and their optimum temperatures for incubation.

It should be understood that the assays run herein with both the enumeration test and PNA test are on microcolonies of microorganisms that develop from the single cells captured on the membranes i.e. one is enumerating the numbers of single organisms in a test sample by detection of colonies that arise by growth division from those same single organisms rather than detecting the individual organisms directly.

After a suitable incubation period for the filter on the medium, the filter is removed from the media, dried, then sprayed with reagents, and subjected to an enumeration test 4.

A preferred enumeration test is an ATP/bioluminescence test. In such a test, the sample is exposed to a suitable permeabilizing agent such as ATP releasing agent from the MicroStar reagent kit (RMLL00000) available from Millipore Corporation of Bedford, Mass. ATP is then detected through the use of a bioluminescence reagent such as Bioluminescence Reagent from the MicroStar reagent kit available from Millipore Corporation of Bedford, Mass. The luminescence is then read visually or digitally through an imagining device such as CCD camera with image processor. One such system is sold as MicroStar™ system, available from Millipore Corporation of Bedford, Mass. By whatever means that is used, the count and location of the microbial colonies detected can be made.

Alternatively, one may use the process of U.S. Pat. No. 5,627,042 the teachings of which are incorporated herein by its entirety. In this process, ATP is extracted from a living organism on a membrane through the use of an extraction agent such as NRB™ available from Lumac, Co. and then subjected to a bioluminescence agent such as Lumit-PM™ from Lumac Co. The luminescence is then measured on a device that detects and records the location of the light emitted by the ATP/reagent reaction. However, this process is not preferred as it actually ruptures the cell wall spilling its contents on to the membrane surface. Even though the membrane has hydrophobic partitions, it can not be guaranteed that some cross contamination will not.

A further alternative is to use a system for enumeration that does not rely on the detection of ATP but uses some other mechanism to determine the presence and the number of organisms. One such system is ScanRDI available from Chemunex. Rather than using ATP, it uses a fluorescent tag that is absorbed by the organisms (fluorescent tag absorption test) and then detected under a fluorescent light.

After the enumeration test, the sample is then subjected to a PNA probe assay 5 for the target organisms. PNA probes are peptide nucleic acid probes (rather than DNA based probe) and are designed to enter a cell and hybridize to a select portion of an RNA or DNA strand of that cell. They may be designed so as to specifically hybridize only to a single species or to an entire genus. The probes contain a tag such as an enzyme, hapten, fluorophore or radioisotope to indicate their presence in the cell. Such probes are available from a variety of sources including Boston Probes, Incorporated of Bedford, Mass. under tradenames such as EcoO6™ probes for the detection of *E. coli* and BacUni™ probes for the simple detection of all bacteria. The method of making and using such probes are taught by U.S. Pat. Nos. 5,714,331; 5,736,336; 5,773, 571; 5,912,145 and 5,985,563; and PCT published applications WO 98/24933 and 99/49293, the teachings of which are hereby incorporated in their entireties.

In this step, the organisms on the same filter are subjected again to a permeabilizing and fixation agents such as ethanol and glutaraldehyde, and PNA probes are applied to the permeable cells. One may select one or more PNA probes to detect one or more species of organisms. Some exist for individual organisms such as *E. coli* or Salmonella sp., *L. brevis*, etc, while others are more universal and simply detect the presence of bacteria or yeast or fungi. After application of the probe(s), the membrane is allowed to sit for a period of time, typically 10 minutes to 1 hour and is then washed to remove any unhybridized probes. Depending upon probes selected and the method used to incorporate a detectable tag on it, one can use X-ray film, instant film, fluorescence, colorimeter or other such device to detect the presence of the tag of the probes which have hybridized to the DNA or RNA of the organism and thereby identify the number and type of each target organism present.

It is preferred to use a chemiluminescent material and then detect the presence of the chemical light by a photograph or a digital imager such as the MicroStar™ system available from Millipore Corporation of Bedford, Mass.

Figure 2:
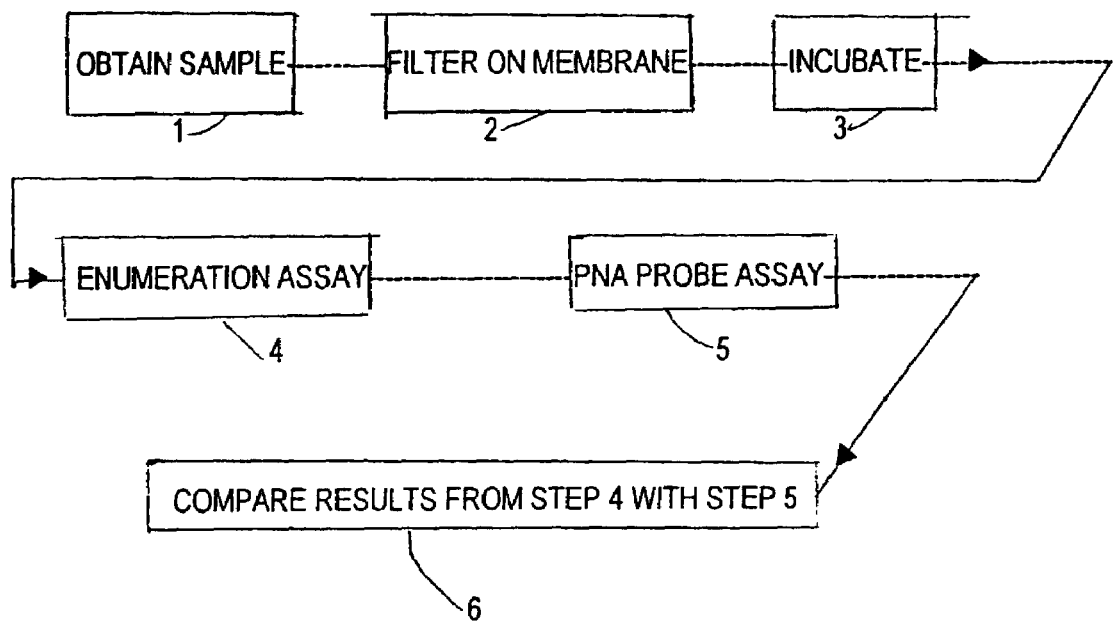
FIG. 2 shows a block diagram of a second preferred embodiment of the present invention.

FIG. 2 shows another preferred embodiment of the present invention. To the extent that the reference numbers indicate the same steps as in FIG. 1, the reference numbers have remained the same.

In this embodiment, after the enumeration and PNA probe steps have been completed, the results of each test is compared with each other to determine whether there are indications of colonies of organisms on one test in a certain location which are not found in the same location with the other test. This allows one to eliminate any false positives from the results. This is particularly true with the PNA probe test which sometimes identifies a location as containing a colony of an organism when further analysis indicates that no colony is present at that location. The simplest means for doing this is use a MicroStar™ system available from Millipore Corporation of Bedford, Mass. and to superimpose or view in parallel the two images. Alternatively, one can use a software program to automatically compare the two test results and discount any spot not found in the same location on both tests.

This is a particularly useful in applications where the enumeration and identification of microorganisms is required or desired.

EXAMPLE

Tests were conducted to determine whether the present process could be used to enumerate and distinguish two closely related microorganisms, *Escherichia coli* and *Salmonella choleraesuis*.

Pure cultures of *Escherichia coli* and *Salmonella choleraesuis* were diluted to an estimated 50 colony forming units per 100 μl in a sterile 0.85% saline solution. Some of the two cultures were mixed together and filtered as a mixture while the rest were filtered separately through MicroStar™ filter discs in a glass filter holder, both available from Millipore Corporation of Bedford, Mass.

The membranes were then incubated for six hours. The membranes from each set (mixed as well as the individual organisms) were subjected to an ATP-bioluminescence enumeration assay using the MicroStar™ Reagent Kit RMLL00000 available from Millipore Corporation of Bedford, Mass. to determine the number of colonies on each membrane. Samples of each set were also stored on the traditional media growth plates and incubated for overnight at 30° C.

The same membranes were then subjected to a PNA probe assay using probes *E. coli*-specific Eco06™ probes available from Boston Probes, Inc. of Bedford, Mass.) and to a PNA probe assay for determining all bacteria including the two used in this test (BacUni™ probes available from Boston Probes, Inc. of Bedford, Mass.).

On the membranes where the blend of organisms were filtered onto the same membrane, the number of colonies detected using the PNA probe specific for *E. coli* equaled the number of *E. coli* cells filtered, while the colonies observed with the universal bacteria probe equaled the sum of both organisms present.

In contrast, equivalent numbers of colonies were detected on the membranes that filtered only the *E. coli*, using either probe. The membranes that filtered only the *S. choleraesuis* could only be detected using the universal probe.

Additionally, the organisms detected by the PNA probes were matched to the locations found by the ATP-bioluminescence assay so as to eliminate any false positives caused by the membrane or its contamination.

These results were consistent with the numbers of colonies detected by the ATP assays or on the growth control plates. This demonstrates that a specific microbial species can be detected and enumerated using a combination of ATP and PNA probe assays on the same membrane.

What we claim:

1. A process for enumerating and identifying microorganisms comprising: (a) filtering a liquid sample through a membrane suitable for the retention of microorganisms, (b) incubating said membrane with any microorganisms, (c) applying an enumeration test to the surface of said membrane to enumerate the colonies of microorganisms that are present, and counting the number present, (d) applying a PNA hybridization to the microorganisms on said membrane to determine the presence/absence of one or more specified microorganisms, and counting the number detected, and (e) matching the organisms found by said enumeration test to the locations of the colonies of organisms found by said PNA hybridization step and eliminating those locations found by the PNA hybridization which do not correspond to the locations found by the enumeration test.

2. The process of claim 1 wherein the liquid sample is from 50 to 1000 milliliters, the membrane is selected from the group consisting of PVDF membrane having hydrophilic areas separated by hydrophobic partitions, the membranes are incubated for 1 to 24 hours at a temperature of from about 24° C. to about 40° C. and the enumeration test is selected from the group consisting of an ATP-bioluminescence test and a fluorescent tag absorption test.

3. The process of claim 1 wherein the enumeration test is an ATP/bioluminescence test and is read by a digital imaging system.

4. The process of claim 1 wherein the PNA hybridization step is read by a process selected from the group consisting of X-ray film, instant film, visual detection of a colorimetric reaction on the membrane, visual detection of a fluorescent tag or by digital imaging.

5. A process for enumerating and identifying microorganisms comprising (a) filtering a liquid sample through a membrane suitable for the retention of microorganisms, (b) incubating the membrane with any microorganisms, (c) registering the membrane so as to indicate a specific point along one edge of the membrane, (d) applying an enumeration test to the surface of the membrane to enumerate the colonies of microorganisms which are present, and counting the number present, (e) applying a PNA hybridization to the microorganisms on said membrane to determine the presence/absence of one or more specified microorganisms, and counting the number detected and (f) matching the organisms found by the enumeration test to the locations of the organisms found by the PNA hybridization through the use of the registration mark and eliminating those locations found by the PNA hybridization which do not correspond to the locations found by the enumeration test.

6. The process of claim 5 wherein the liquid sample is from 50 to 1000 milliliters, the membrane is selected from the group consisting of PVDF membrane having hydrophilic areas separated by hydrophobic partitions and the membranes are incubated from about 1 to about 24 hours at a temperature of from about 24° C. to about 40° C.

7. The process of claim 1 wherein the membranes are incubated from about 3 to about 8 hours.

8. The process of claim 5 wherein the membranes are incubated from about 3 to about 8 hours.

9. The process of claim 5 wherein the enumeration test is an ATP/bioluminescence step that is read by a digital imaging system.

10. The process of claim 5 wherein the PNA hybridization is read by a process selected from the group consisting of X-ray film, instant film, visual detection of a colorimetric reaction on the membrane, visual detection of a fluorescent tag or by digital imaging.

11. The process of claim 5 wherein the enumeration test is a fluorescent tag absorption test.

* * * * *

UNITED STATES PATENT AND TRADEMARK OFFICE
CERTIFICATE OF CORRECTION

PATENT NO.        : 7,588,886 B2                              Page 1 of 1
APPLICATION NO. : 10/181517
DATED             : September 15, 2009
INVENTOR(S)       : Young et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 596 days.

Signed and Sealed this

Twenty-first Day of September, 2010

David J. Kappos
*Director of the United States Patent and Trademark Office*